United States Patent [19]

Anderson

[11] 4,101,276
[45] Jul. 18, 1978

[54] METHOD AND APPARATUS FOR SIGNALLING THE INTRODUCTION OF CHEMICAL REACTION COMPONENTS INTO A CHEMICAL ANALYZING SYSTEM

[75] Inventor: Robert J. Anderson, Orange, Calif.

[73] Assignee: Beckman Instruments, Inc., Fullerton, Calif.

[21] Appl. No.: 692,159

[22] Filed: Jun. 2, 1976

[51] Int. Cl.² ............... G01N 21/38; G01N 33/16
[52] U.S. Cl. ............................. 23/230 B; 23/253 R; 356/39; 250/461 B
[58] Field of Search ............... 23/230 B, 253 R; 356/39, 73; 73/64.1; 250/461, 461 B

[56] References Cited

U.S. PATENT DOCUMENTS

| | | | |
|---|---|---|---|
| 3,307,392 | 3/1967 | Owen et al. | 73/64.1 |
| 3,450,501 | 6/1969 | Oberhardt | 23/230 B X |
| 3,458,287 | 7/1969 | Gross et al. | 23/230 B |
| 3,593,568 | 7/1971 | Schmitz et al. | 73/64.1 |
| 3,710,933 | 1/1973 | Fulwyler et al. | 356/73 |
| 3,850,525 | 11/1974 | Kaye | 356/73 |
| 3,905,767 | 9/1975 | Morris et al. | 23/230 B |
| 3,971,951 | 7/1976 | Rikukawa et al. | 250/461 B |
| 3,974,269 | 8/1976 | Maley | 23/230 B X |

Primary Examiner—Robert M. Reese
Attorney, Agent, or Firm—Robert J. Steinmeyer; Robert R. Meads; John R. Shewmaker

[57] ABSTRACT

A system for chemically analyzing antigens or antibodies by initiating an antigen-antibody reaction in a reaction zone and measuring the light scattered by a precipitate produced by the reaction to determine the antigen or antibody concentration. In order to signal the start of the reaction, a fluorescent tagging substance is included with at least the last antigen or antibody reaction component introduced into the reaction zone. The fluorescent tagging substance does not enter into the antigen-antibody reaction and is selected to emit light in a bandwidth spectrally separated from the light scattered by the precipitate. The reaction zone is monitored for the presence of the tagging substance, and when the substance is detected a trigger signal is generated to signal the start of the reaction. By including a tagging substance with each component of the reaction and by monitoring the reaction zone for the presence of each tagging substance, a trigger signal is generated only if each reaction component is present.

16 Claims, 5 Drawing Figures

METHOD AND APPARATUS FOR SIGNALLING THE INTRODUCTION OF CHEMICAL REACTION COMPONENTS INTO A CHEMICAL ANALYZING SYSTEM

BACKGROUND OF THE INVENTION

1. Field of the Invention

The present invention relates to the detection of chemical reaction components and, more particularly, to the detection of components introduced into a reaction zone in order to signal the beginning of a chemical reaction. The invention is particularly useful in the field of non-isotopic immunoassay for detecting the components of antigen-antibody reactions.

2. Description of the Prior Art

A common method for assaying antigens and antibodies is based on the fact that antigens react with their corresponding antibodies to produce a precipitate. The quantity of precipitate produced in an antigen-antibody reaction is proportional to either the antibody concentration or the antigen concentration, depending on which is present in excess. That is, for excessive antigen, the quantity of precipitate is proportional to the antibody concentration while, for excessive antibody, the quantity of precipitate is proportional to the antigen concentration. The quantity of precipitate produced is commonly determined with nephelometric techniques by measuring the extent to which the precipitate scatters a beam of light directed at the zone of the antigen-antibody reaction. However, a given quantity of precipitate may correspond to two possible values of antigen concentration depending on whether the antibody or the antigen is present in excess.

U.S. patent application Ser. No. 692,089, filed concurrently herewith, in the name of Robert J. Anderson et al. and entitled A System For Specific Serum Protein Analysis, discloses a system for the analysis of antigens and antibodies which measures the maximum value of the rate of change of the scattered light signal generated as the precipitate is formed during an antigen-antibody reaction. Significantly, as set forth in detail in the application, the time at which such maximum rate of change occurs following initiation of the antigen-antibody reaction has been found to indicate which of the two reaction components is present in excess. In other words, antigen excess is distinguished from antibody excess by observing the time after the start of the reaction at which the maximum rate of change of the scattered light signal occurs. Knowing which reaction component is present in excess enables the measured quantity of precipitate to be correlated to the correct one of the two possible values of antigen concentration. In order to measure the elapsed time between the start of the reaction and the maximum rate of change of the scattered light signal, it is necessary to first establish the reaction starting time. In this manner a timing clock can be started simultaneously with the reaction and used to measure the elapsed time to the maximum rate of change value.

Beyond the assay of antigens and antibodies, there are additional areas of chemical analysis for which it is necessary to ascertain the starting time of a chemical reaction. For example, in blood plasma prothrombin time determinations, a blood plasma sample and a clotting reagent are combined, and a measurement is made of the time required for the plasma sample to coagulate (clot). See for example U.S. Pat. Nos. 3,450,501 (Oberhardt) and 3,593,568 (Schmitz). Typically, the clotting is measured by a photodetector which detects light scattered by the clot as the clot forms and generates an electrical signal having a value which indicates the extent of clot formation. Obviously, in order to accurately measure the elapsed clotting time, it is first necessary to establish the starting time of the clotting reaction.

In the analysis of antigen-antibody reactions, as described in the aforementioned copending patent application, an operator manually pipettes the antigen and antibody reaction components, one at a time, into a reaction cell. Manual pipetting is also employed in prothrombin time determinations in the aforementioned Oberhardt and Schmitz patents. Oberhardt teaches that a timer may be started at the beginning of the reaction by means of a switch activated by depressing the pipette plunger. In this approach, a mechanical switch is attached to the pipette plunger, and as an operator depresses the plunger to eject the reaction component from the pipette, the switch is closed and completes a trigger circuit for signalling the start of the reaction. While manual switch triggering is satisfactory for some purposes, it is subject to a high degree of operator error. For example, if for some reason the pipette is empty, triggering will still take place when the pipette plunger is depressed even though nothing is actually ejected from the pipette. Moreover, if an incorrect reaction component is picked up in the pipette, triggering will still take place when this component is ejected into the reaction zone. Beyond this, it is possible to accidentally trip the switch and thus actuate the trigger circuit during an incorrect part of the analysis cycle. In order to prevent such accidental triggering, it is necessary to incorporate an "arming" switch on the analyzer control panel which prevents triggering unless the arming switch is actuated. However, an arming switch increases the operating and mechanical complexity of the system. Moreover, if the switch is left unarmed when the sample is introduced, the trigger will not function and the assay must be repeated.

A second approach for signalling the start of a chemical reaction is also suggested for the blood clotting reactions in the aforementioned Oberhardt and Schmitz patents. In the determination of blood clotting times, a detector monitors the scattering of light by the clot and generates a signal having a value indicating the extent of clot formation. In the two mentioned patents, when a reaction component is ejected into the reaction zone, a small upset or variation in the scattered light signal is detected to signal the start of the reaction. Unfortunately, this approach is often difficult to implement. First, the small variation in the scattered light signal is not a consistent and repeatable phenomenon. More importantly, and particularly as regards the nephelometric assay of antigen-antibody reactions, the scattered light signal ideally should exhibit no perceptible change at the time the last reaction component is introduced. This is because, with proper preparation, the antigen and antibody reaction components are essentially transparent and, thus, produce little if any light scattering. Thus it is evident that the scattered light signal does not provide an accurate measure of the start of the antigen-antibody reaction since the signal will not change perceptibly until some time interval after the start of the reaction when the precipitate begins to form.

From the above, it is evident that a need exists for a simple and dependable method and apparatus for monitoring components of a chemical reaction and for signalling the start of the reaction. The present invention fulfills these needs.

SUMMARY OF THE INVENTION

The present invention resides in a novel method and apparatus for monitoring the components of a chemical reaction to signal the introduction of the components into a reaction zone and signal the start of the chemical reaction in a manner which overcomes the disadvantages of the prior art. To these ends, a tagging substance is incorporated at least in the last reaction component introduced into the reaction zone. The tagging substance is chemically isolated from the reaction in the reaction zone. Means are provided for monitoring the reaction zone for the presence of the tagging substance and, upon detecting the substance, for signalling the start of the chemical reaction.

In a preferred form, the tagging substance is fluorescent substance . In a system which measures an optical characteristic of the reaction, such as the scattering of light, the fluorescent tagging substance is selected to emit light in a bandwidth spectrally separated from the scattered light. Since the tagging substance is chemically isolated from the reaction and the light issuing therefrom is spectrally separated from the scattered light, the tagging substance does not interfere with the detection of scattered light. In another embodiment, the tagging substance is added to more than one component of the chemical reaction, and means are provided for monitoring the reaction zone for each tagging substance and for signalling the start of the reaction only upon detection of all tagged components of the reaction.

DESCRIPTION OF THE PREFERRED EMBODIMENTS

Figure 1:
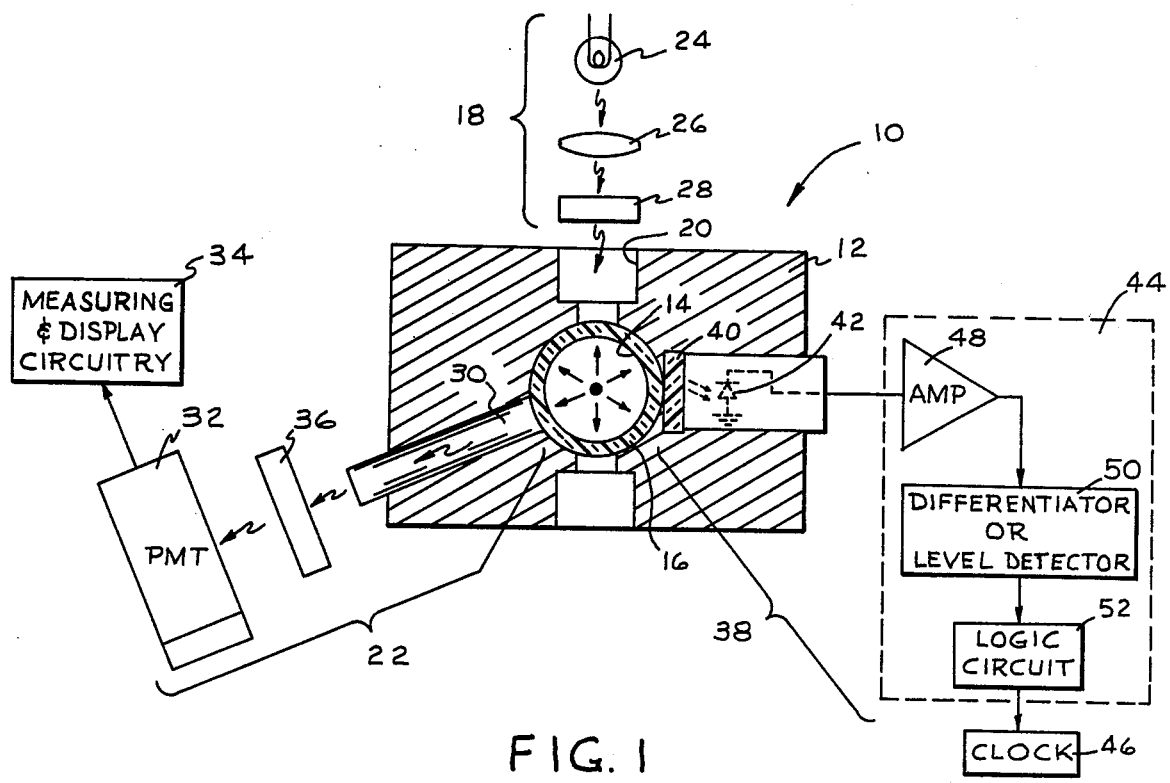
FIG. 1 is a diagrammatic, cross-sectional view, taken in a generally horizontal plane, through the reaction cell of an antigen-antibody analyzing system and in addition illustrates in block form apparatus for signalling the start of a reaction in the reaction zone.

As shown in the drawings for purposes of illustration, and in particular FIG. 1 thereof, the present invention is embodied in a chemical analyzing system having a sample cell 10 defined by a block 12 of insulating material having a vertical bore therein defining a reaction chamber or zone 14 for receiving chemical reactants introduced into the sample cell. A bottom portion of the reaction zone is lined with a cylindrical glass liner 16 which permits light transmission through the liner to and from the contents of the reaction zone. For the nephelometric assay of antigen and antibody reaction components, the analyzer includes an optical excitation system 18 for directing a beam of light through an aperture 20 in the insulating block 12 and through the glass liner 16 into the reaction zone together with an optical detection system 22 for detecting light scattered by the contents of the reaction zone.

The excitation system 18 comprises a light source 24, such as an incandescent, tungsten filament lamp, a collimating lens system 26 for collimating the light from the lamp and directing it toward the sample cell 10, and a primary filter 28 for filtering the light passed to the reaction zone.

The detection system 22 comprises a light pipe 30 supported within a bore in block 12 and having one end disposed adjacent the reaction zone for intercepting and collecting light scattered by the contents of the reaction zone and an opposite end for transferring the light collected by the pipe to a suitable detector, such as a photomultiplier tube 32. The output of the photomultiplier is connected to measuring and display circuitry 34 for supplying a suitable record of the scattered light signal. A secondary filter 36 is interposed in the light path between the light pipe and the photomultiplier tube for isolating the wavelengths of the detected scattered light signal.

In the assay of an antigen-antibody reaction, the antigen and antibody reaction components may be injected one at a time into the reaction zone 14 of the sample cell 10 by means of a manually operated pipette. When the antigen and antibody reaction components are combined in the reaction zone, a chemical reaction is initiated which forms a precipitate in the reaction zone. Light from lamp 24 directed at the reaction zone is scattered by the precipitate and the scattered light is detected by the optical detection system 22 and converted into a signal providing a measure of the quantity of precipitate formed and, thus, a measure of the reaction component of interest. However, as previously noted, the quantity of precipitate may correspond to two possible antigen concentration values depending on whether antigen or antibody is present in excess. Antigen excess can be distinguished from antibody excess, however, by measuring the elapsed time between the start of the reaction and the precipitate measurement.

In accordance with a primary aspect of the present invention, a fluorescent tagging substance is included with at least the last reaction component injected into the reaction zone 14, and the reaction zone is monitored for the presence of the fluorescent substance by a signalling system 38. Since the antigen-antibody reaction begins upon introduction of the last reaction component, detection of the tagging substance in the last introduced component indicates the starting time of the reaction.

Signalling system 38 comprises a long pass cut-on filter 40 disposed adjacent the reaction zone 12 and a photodetector 42, such as a light responsive photodiode, for receiving and detecting light passed by filter 40. The output signal from the detector 42 is, in turn, coupled to a trigger circuit 44 for generating a trigger signal for triggering other circuit components, such as a timing clock 46. In this manner, when the reaction component which includes the fluorescent tagging substance is injected into the reaction zone, detector 42 and trigger circuit 44 respond to light emission from the fluorescent substance to trigger the timing clock at the start of the antigen-antibody reaction.

The trigger circuit 44 may comprise an amplifier 48 for amplifying the photodiode output signal, a differentiator 50 responsive to the amplified signal for generating a pulse signal, and a logic circuit 52 responsive to the pulse signal from the differentiator for generating a trigger signal which starts the timing clock 46. Alternatively, the differentiator 50 may be replaced by a threshold or level detector which supplies an output pulse signal to logic circuit 52 when the amplified photodiode output signal reaches a predetermined value. These features of the trigger circuit are all of well known design.

For proper operation of the signalling system 38, the light which is absorbed by and emitted from the fluorescent tagging substance should not interfere with the scattered light which is measured to assay the antigen or antibody reaction components. Thus, the tagging substance should neither absorb nor emit light in the spectral band used to measure the antigen-antibody scattered light signal. In addition, accurate measurement of the light emitted by the tagging substance requires that such emitted light be detected in a spectral band isolated from the spectral band used to excite the tagging substance. To achieve these ends, the fluorescent tagging substance, the primary filter 28, the secondary filter 36, and cut-on filter 40 are selected to define three separate spectral bands. The first spectral band is used to excite and measure the scattered light from the precipitate. The second spectral band defines the absorption band of the fluorescent tagging substance. The third spectral band defines the band of fluorescent emission from the tagging substance.

Figure 2:
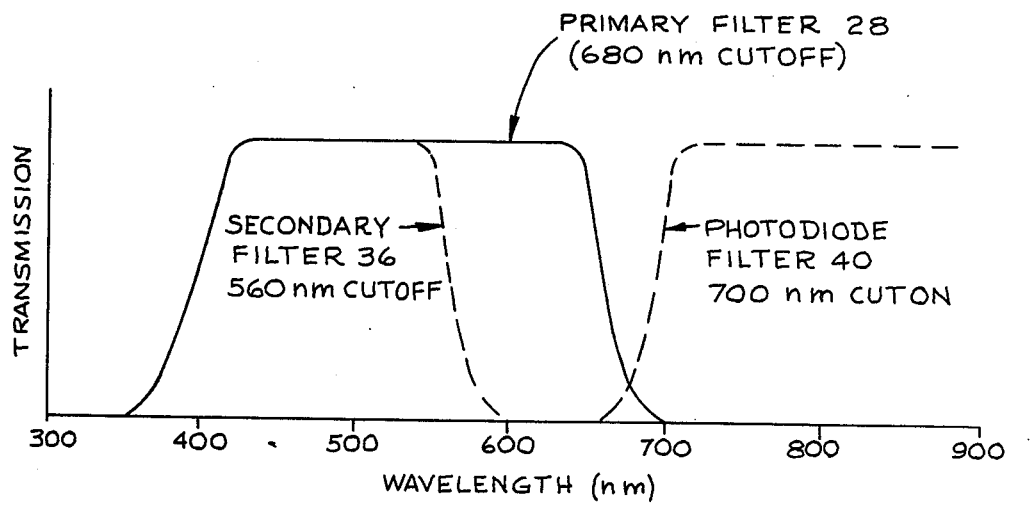
FIG. 2 is a graphical plot of optical transmission vs. wavelength which illustrates the bandpass characteristics of the filters in the present system.

Primary filter 28 determines the spectral band of light which impinges on the reaction zone and is scattered by the precipitate therein. Moreover, filter 28 establishes the spectral band which excites the fluorescent tagging substance. In the preferred embodiment, as illustrated in FIG. 2, the primary filter 28 is transmissive between approximately 400 nm and 680 nm. Light outside of this band, that is having a wavelength less than 400 nm or greater than 680 nm is rejected by the filter 28 and cannot reach the reaction zone.

Secondary filter 36 adjacent photomultiplier tube 32 isolates the wavelengths of the scattered light detected by the photomultiplier 32. As illustrated in FIG. 2, the secondary filter has a cut-off wavelength of approximately 560 nm, so that wavelengths greater than this value are rejected by the secondary filter and cannot reach the photomultiplier.

Long pass filter 40 in the signalling system 38, has a high cut-on wavelength of approximately 700 nm, so that all wavelengths below this value are rejected by the filter and prevented from reaching the photodiode 42.

Figure 3:
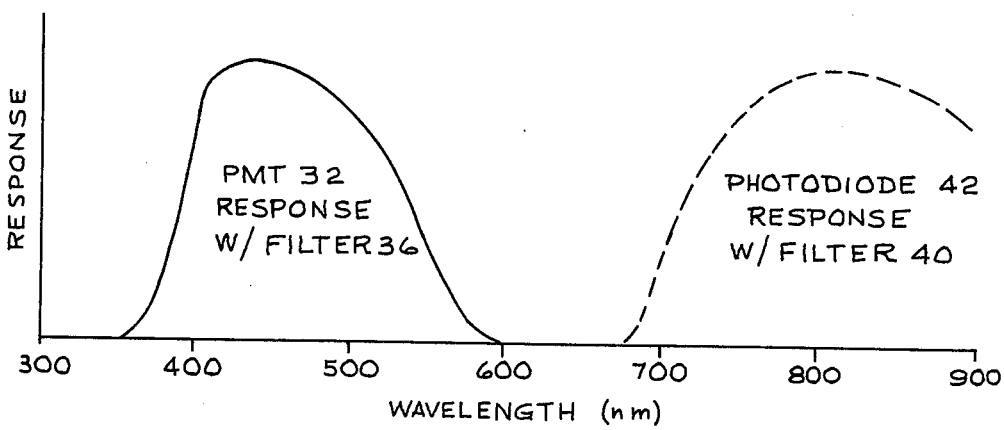
FIG. 3 is a plot of optical response vs. wavelength and illustrates the spectral separation between the response of the photomultiplier tube and photodiode in the system.

FIG. 3 illustrates the response of photomultiplier tube 32 and photodiode 42 when using the above filters. Spectral separation is achieved between the photomultiplier response, which measures the quantity of precipitate formed, and the photodiode response, which indicates the presence of the fluorescent tagging substance.

In addition to the spectral seperation between the photomultiplier response measuring the scattered light signal and the photodiode response measuring the fluorescent tagging substance, it is important that the tagging substance be chemically isolated from the antigen-antibody reaction so that the tagging substance does not affect the formation of precipitate and thus affect the value of the scattered light signal. In addition, the tagging substance itself should not introduce substantial turbidity into the reaction zone which would also affect the scattered light signal value.

Figure 4:
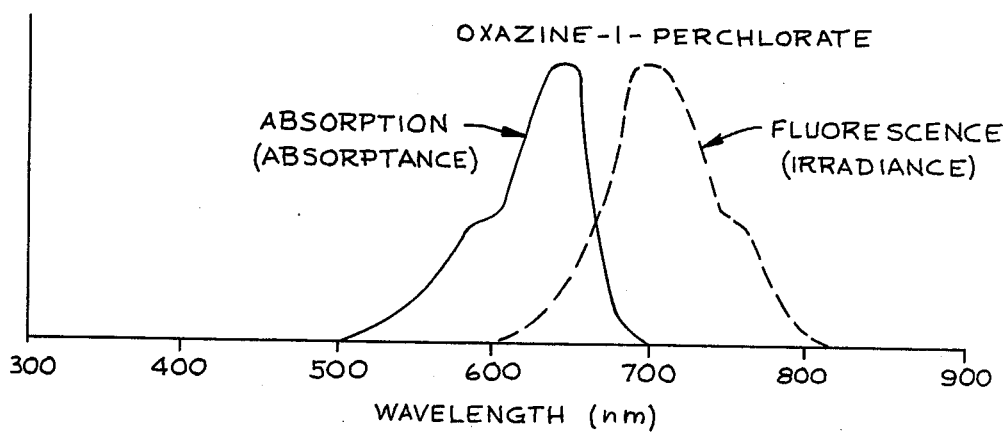
FIG. 4 is a plot of optical absorption and fluorescent emission vs. wavelength for one fluorescent tagging substance.

One suitable fluorescent tagging substance for use with the filters of FIG. 2, is oxazine-1-perchlorate (O-1-P), which has a molecular weight of 423.90 and a peak extinction coefficient at 645 nm of $\epsilon = 12.5 \times 10^4$ liters/mole cm. The absorption and fluorescent emission characteristics of this substance are illustrated in FIG. 4. As shown, oxazine-1-perchlorate absorbs light in a spectral band between approximately 550 and 650 nm and fluoresces in a band between approximately 650 and 800 nm. It should be noted that the absorption and emission bands of this substance are spectrally separated from one another as well as from the band for detecting the scattered light signal. Thus, absorption and emission of the tagging substance does not interfere with or overlap with the scattered light signal and the tagging substance does not introduce substantial turbidity into the reaction zone. Moreover, the tagging substance is chemically inactive with respect to the antigen-antibody reaction. As a result, the tagging substance is not a source of interference in the detection of the scattered light signal.

EXAMPLES

A stock solution of oxazine-1-perchlorate was prepared by dissolving 50 mg of the O-1-P in 100 ml of deionized water (i.e. $1.18 \times 10^{-3}$ moles/liter).

A stock buffer solution was prepared by combining 150 mmoles of sodium chloride and 4 gms of polyethylene glycol 6000 in 100 ml of deionized water.

Three different working solutions comprising a combination of the O-1-P stock solution and the stock buffer solution were prepared in dilution ratios of stock solution to total solution of 1:40, 1:101, and 1:201.

Monospecific goat antiserum (antibody) with a titer level of 120-140 mg antigen bound per 100 ml prepared against human C'3-Complement (or some other protein, e.g. IgG, IgA, or IgM, etc.) was diluted with each of the three working solutions containing the O-1-P tagging substance in the ratio of 1 part antiserum plus 3 parts working solution.

A new working solution without O-1-P was prepared comprising 150 mM sodium chloride in deionized water for diluting serum (antigen) samples.

A control serum (designated RSC-19) was diluted with the new working solution in the following ratios of serum to working solution — 1:199, 1:39, 1:14, and 1:6. (The RSC-19 was known to contain 350 mg/100 ml of C'3-Complement).

Each of the three antibody solutions containing the tagging substance O-1-P were combined with each of the serum solutions in a reaction cell. For each antibody and antigen reaction component so combined, the reaction cell was filled with 700 $\mu l$ of the stock buffer solution and 50 $\mu l$ quantities each of the antigen and antibody solutions were pipetted manually one at a time into the stock buffer solution in the cell. The antibody solution was pipetted last, and the change in the voltage signal supplied by photodiode 42 was measured. With a 640 nm primary filter 28 in position, the voltage change for the antibody dilutions of 1:40, 1:101, and 1:201 was respectively 5 volts, 2 volts, and 1.1 volts. With a 620 nm primary filter 28, the voltage change for the same dilutions was 2.8 volts, 1.1 volts, and 0.5 volts, respectively.

In the above example, the fluorescent tagging substance was included in the antibody reaction components, and the antibody component was introduced into the reaction zone last to indicate the beginning of the antigen-antibody reaction. In a further example, the control serum (antigen) was diluted with the different O-1-P working solutions and the antigen component was introduced last into the reaction zone. In this example, the O-1-P tagging substance in the antigen reaction component induced voltage changes at the output of photodiode 42 similar to those produced for the previously described tagged antibody reaction components. Thus the tagging substance works equally well in both the antigen and the antibody reaction components and may be introduced into either one.

In order to ensure that both reaction components are present in the reaction zone, the tagging substance may be included in both the antigen and the antibody reaction components instead of simply in the last reaction component injected into the reaction zone. In this example, the signalling system 38 detects the fluorescent emission from the tagging substance in each reaction component. This is illustrated by the dashed curve in FIG. 5 which shows the increase in the fluorescence signal detected upon introduction separately of the two reaction components. For this example, the differentiator 50 may be replaced by the previously described conventional level detector. The level detector is set to supply an output pulse to the logic circuit 52 for triggering clock 46 only when the fluorescent signal reaches a level indicating that first and second injections have taken place. In this manner, clock 46 is not triggered unless two tagged reaction components are introduced into the reaction zone.

Figure 5:
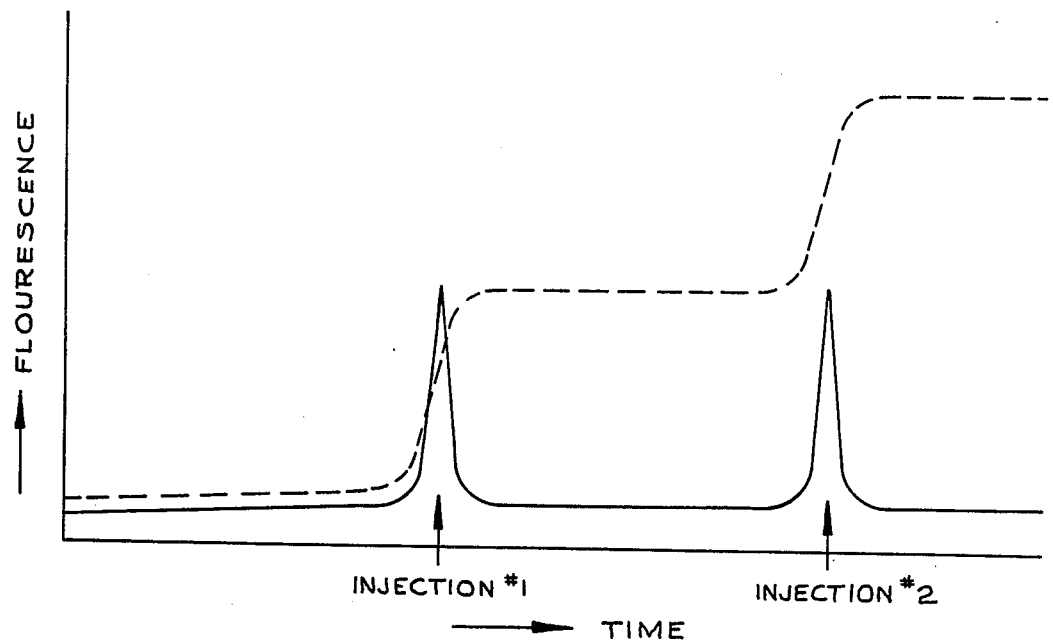
FIG. 5 is a plot of the fluorescence signal vs. time and illustrates the change in the fluorescent signal at times corresponding to the injection of first and second reaction components. The figure also illustrates the derivative of the fluorescence signal at the times of injection.

The solid line in FIG. 5 illustrates the derivative of the fluorescent signal for the first and second injections where differentiator 50 is employed in trigger circuit 44. In such case, logic circuit 52 may comprise a conventional two-stage counter for triggering the clock 46 only in response to the combination of a first and a second pulse from differentiator 50 indicating that the first and second reaction components had been injected into the reaction zone. Of course the counter would automatically reset upon triggering the clock 46 and upon lapse of a predetermined time between input pulses.

In order to prevent first and second injections of the same reaction component from triggering clock 46 in the above embodiment, a different amount of tagging substance may be included in each component. Thus, for example, if the antigen component contained one unit of tagging substance and the antibody component contained two units of tagging substance, then injection of the antigen and the antibody reaction components into the reaction zone would produce a total of three units of tagging substance in the reaction zone. If two antigen components were mistakenly injected, only two units of tagging substance would be present. If two antibody components were mistakenly injected, then four units of tagging substance would be present. Thus, for two injections, the correct combination of three units of tagging substance is present only if one injection is the correct antigen component and the other injection is the correct antibody component. In this embodiment, a level detector 50 having a predetermined operating "window" is employed and is set to generate an output pulse only for a voltage response by photodiode 42 corresponding to three units of tagging substance.

It will be appreciated from the foregoing that the present invention represents an improvement in the methods and apparatus heretofore employed for monitoring introduction of chemical reaction components into a reaction zone and for signalling the start of the chemical reaction. Incorporating a tagging substance in at least one of the reaction components eliminates the need to manually actuate a trigger circuit upon introduction of the component. In addition, maintaining chemical isolation between the chemical reaction and the tagging substance enables a characteristic of a reaction, such as the scattering of light by a product of the reaction, to be measured without interference from the tagging substance. Moreover, the need to rely on such scattered light signal to additionally signal the introduction of reaction components is eliminated. When a fluorescent tagging substance is employed, interference of the tagging substance with the measured scattered light signal is eliminated by maintaining spectral separation between the light emitted from the tagging substance and the scattered light. Moreover, it will be apparent that while a preferred embodiment of the invention has been illustrated and described, various modifications may be made without departing from the spirit and scope of the invention as defined in the following claims.

What is claimed is:

1. In a method of combining components of a chemical reaction which includes the steps of introducing the reaction components into a reaction zone to initiate the chemical reaction and measuring a characteristic of the reaction, the improved method of signalling the start of the chemical reaction comprising the steps of:
   prior to initiating the chemical reaction adding a tagging substance to at least the reaction component last introduced into the reaction zone, the tagging substance remaining chemically isolated from the reaction; and
   monitoring the reaction zone for the presence of the tagging substance and upon detecting the tagging substance generating a signal indicating the start of the chemical reaction.

2. The method of claim 1 wherein the tagging substance is added to at least an antigen or antibody component of an antigen-antibody chemical reaction.

3. The method of claim 1 including the steps of:
   adding the tagging substance to a second reaction component in addition to said last introduced reaction component; and
   monitoring the reaction zone for the presence of each tagging substance and upon detection of both generating the signal indicating the start of the chemical reaction.

4. The method of claim 3 wherein the tagging substance is added to the first and second reaction components in different relative amounts and the reaction zone is monitored for the presence of the unique combination of the combined different relative amounts of the tagging substance.

5. The method of claim 1 wherein:
   the tagging substance is a fluorescent substance; and
   the step of monitoring includes detecting light emitted by the fluorescent substance to signal the start of the chemical reaction.

6. The method of claim 5 wherein the fluorescent substance is oxazine-1-perchlorate.

7. The method of claim 5 wherein:

the step of measuring a characteristic of the reaction measures an optical characteristic thereof in a first spectral band;

the fluorescent tagging substance is selected to emit light in a third spectral band separate from said first spectral band; and the step of monitoring includes detecting light in the third spectral band.

8. The method of claim 7 wherein the fluorescent tagging substance is further selected to absorb light in a second spectral band separate from the first and third spectral bands.

9. The method of claim 8 wherein the fluorescent tagging substance is added to a component of an antigen-antibody chemical reaction, and said optical characteristic is light scattered by a precipitate formed during the reaction.

10. An electrochemical system for detecting the combining of components of a chemical reaction comprising:

a reaction chamber for serially receiving a plurality of said components for a chemical reaction within the chamber;

means operatively coupled to said chamber for measuring a characteristic of said chemical reaction;

a tagging substance in at least a last one of said components received in said chamber and chemically isolated from said reaction;

separate means operatively coupled to said chamber and insensitive to said characteristic of said chemical reaction for detecting said tagging substance;

triggering means responsive to a detection of said tagging substance for generating an electrical signal indicative of a combining of said components and a start of said chemical reaction;

electrical signal responsive means; and means for supplying said electrical signal to said electrical signal responsive means.

11. The system of claim 10 wherein the measuring means measures an optical characteristic of the reaction;

the tagging substance is a fluorescent substance which fluoresces in a spectral band separate from that of the optical characteristic of the reaction; and the detecting means detects fluorescent light issuing from said tagging substance to the exclusion of said optical characteristic.

12. The system of claim 10 wherein said electrical signal responsive means includes a clock; and said supplying means supplies said electrical signal as a triggering input to start said clock.

13. A nephelometric chemical analyzer comprising:

a reaction chamber for receiving components for a chemical reaction within the chamber;

excitation means for directing a beam of light having first and second separate spectral bands into the reaction chamber;

detection means for detecting light scattered by the contents of the reaction chamber within said first spectral band to measure a scattered light characteristic of the reaction for nephelometric analysis;

a fluorescent tagging substance in at least a last one of said components introduced into the reaction chamber and chemically isolated from the chemical reaction, said fluorescent tagging substance absorbing light in said second spectral band and emitting light in a third spectral band separate from each of said first and second spectral bands;

separate means operatively coupled to said reaction chamber and insensitive to said scattered light characteristic in said first spectral band for detecting fluorescent light issuing from the fluorescent tagging substance in said third spectral band;

triggering means responsive to a detection of the tagging substance for generating an electrical signal indicative of a combining of said components and start of said chemical reaction;

a clock; and means for supplying said electrical signal as a triggering input to start said clock.

14. The analyzer of claim 13 wherein said excitation means includes a source of light and primary filter means for intercepting light from the light source and for passing light in said first and second spectral bands into the reaction chamber while rejecting light in said third spectral band.

15. The analyzer of claim 13 wherein said detection means includes a detector, and secondary filter means for intercepting scattered light from the reaction chamber and for passing light within said first spectral band to said detector while rejecting light in said second and third spectral bands.

16. The apparatus of claim 13 wherein said separate means includes a detector, and filter means for intercepting light from the reaction chamber and for passing light in said third spectral band to said detector while rejecting light in said first and second spectral bands.

* * * * *